United States Patent [19]

Badawi

[11] Patent Number: 5,320,619
[45] Date of Patent: Jun. 14, 1994

[54] LASER DOSIMETER AND POSITIONER, AND METHODS OF CONSTRUCTING AND UTILIZING SAME

[76] Inventor: Radwan A. Badawi, 1718 Ano Nuevo, Diamond Bar, Calif. 91765

[21] Appl. No.: 813,252

[22] Filed: Dec. 24, 1991

[51] Int. Cl.⁵ .................................. A61B 17/36
[52] U.S. Cl. .............................. 606/10; 607/89
[58] Field of Search ............... 128/395, 396, 397, 398; 604/116, 117; 606/2–6, 9–13, 16–19, 32, 41, 96–98, 172, 102; 33/511, 512, 636–641; 433/72–75

[56] References Cited

U.S. PATENT DOCUMENTS

| | | | |
|---|---|---|---|
| 1,213,001 | 1/1917 | Philips | 604/117 |
| 1,831,813 | 11/1931 | Levedahl | 606/96 |
| 5,125,923 | 6/1992 | Tanner et al. | 606/10 |

Primary Examiner—Stephen C. Pellegrino
Assistant Examiner—M. Peffley
Attorney, Agent, or Firm—Irving M. Weiner; Joseph P. Carrier; Pamela S. Burt

[57] ABSTRACT

An apparatus for accurately positioning a laser tool at multiple distances relative to an object to be treated with the laser tool comprises an adjustable distance guide such as a flat body, an adaptor for securing the flat body to the laser tool and an adjustable incremented member which can be selectively, resiliently disposed at various predetermined lengths projecting away from the flat body. The positioning apparatus may be provided in a kit together with a set of predetermined, standardized specifications for using the apparatus together with the laser tool for achieving various different treatment effects, and a set of blank forms for generating additional specifications. A method is disclosed for utilizing such kit.

10 Claims, 1 Drawing Sheet

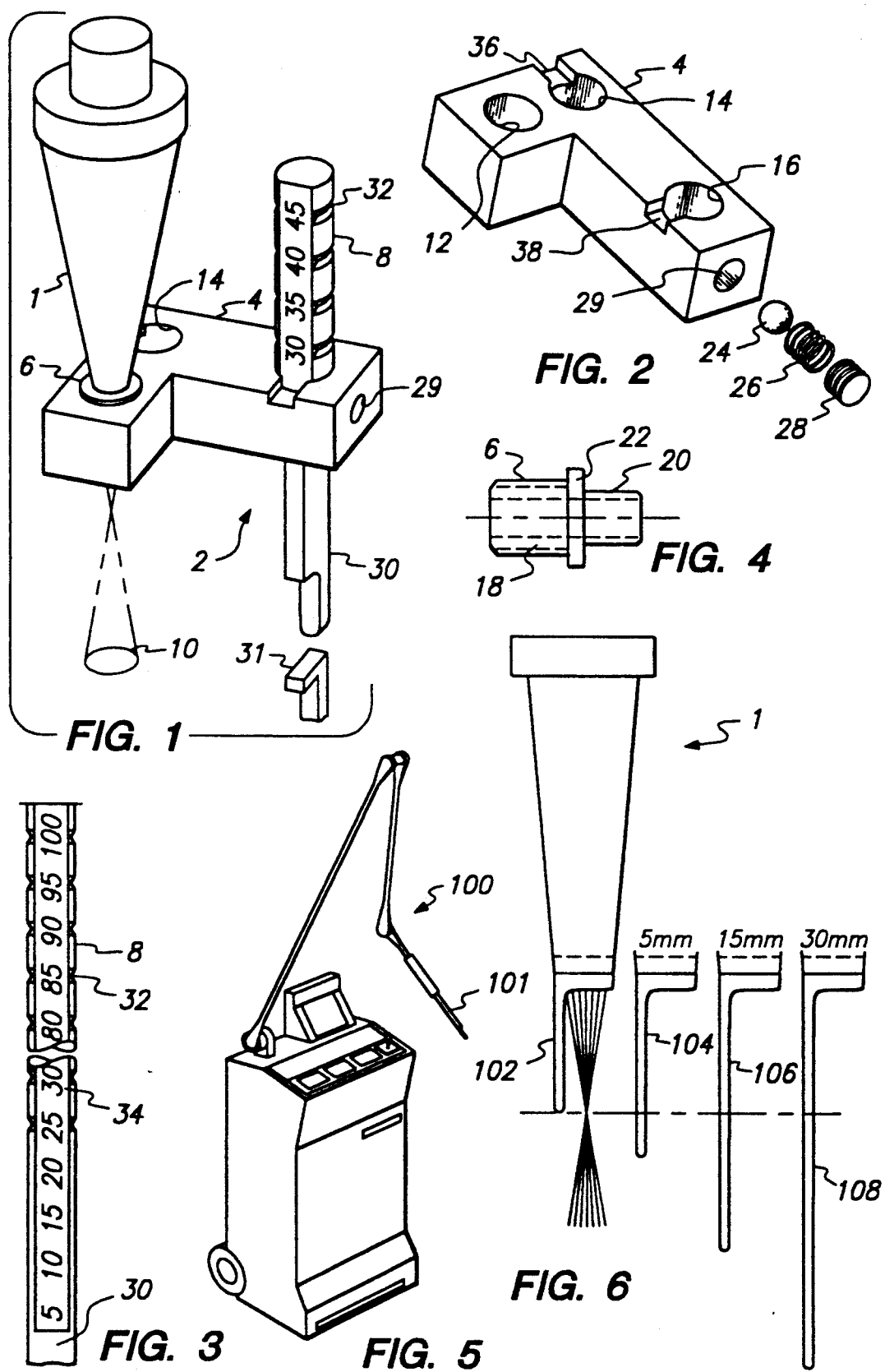

LASER DOSIMETER AND POSITIONER, AND METHODS OF CONSTRUCTING AND UTILIZING SAME

BACKGROUND OF THE INVENTION

1. Field of the Invention

The present invention pertains to a dosimeter and a positioner for a laser tool such as a medical laser with a hand held hand piece. More particularly, the present invention pertains to a novel dosimeter and a positioning apparatus to be use with laser tools so that such tools may be efficiently and accurately used to achieve multiple, distinct treatments of objects to be treated with the laser tools.

2. Description of Relevant Art

There are many known laser tools, including many used for medical purposes, and it is known to treat objects in various ways using such known laser tools. For example there are several known medical lasers including $CO_2$ lasers, ND-YAG lasers, KTP lasers, and argon lasers; and it is known to use such medical lasers in different modes including continuous wave mode where the laser beam is focused at the point of contact for cutting tissue and vaporization mode where the laser beam is not focused at the point of contact for performing medical procedures other than cutting, such as vaporizing a wart, undermining during facelift or blepharoplasty, etc.

It is often difficult to achieve a desired treatment effect, however, because most of the known laser tools are held and manipulated by hand, whereby it is difficult to precisely control many operational parameters of the laser tool during any given operation. Such operational parameters include target distance from the laser tool (the output lens thereof) to the object being treated, the power output of the laser tool, and the speed at which the laser tool is moved relative to the object.

In relation to medical laser tools, the factor of distance control has been partially solved by laser manufacturers who supply a distance guide which attaches the output tip of the laser tool and projects outwardly therefrom by a set distance corresponding to the focal length of the laser output lens with reference to FIG. 5, there is shown a conventional medical laser apparatus having a distance guide 101 on the output tip thereof. Thus, an operator using the medical laser will know that the laser beam output from the laser will be focused (and thus at its maximum intensity) on the tissue being treated when the projecting tip of the distance guide is also in contact or substantially in contact with the tissue.

As will be understood, however, such known distance guides are only useful when the distance guides are being used in a continuous wave mode for performing incisions, and not for the many other procedures involving use of a laser in its vaporization mode. Thus laser surgeons currently have little control over the very significant parameter of distance between the output tip of the laser tool and the tissue specimen being treated. Therefore such surgeons tend to perform a given procedure at different distances from day to day, and even from moment to moment during the same setting procedure. Such lack of distance control leads to inconsistent results, and to more significant problems such as scarring.

Additionally, such known distance guides do not otherwise assure a proper result or effect in any given operation, and do not assure consistently good results in similar operations, because such distance guides do not control the other significant operational parameters during a given operation, whether the laser is used in a continuous wave mode or a defocused mode.

The present invention has been developed to overcome the inadequacies and other disadvantages of known positioning devices for laser tools, and to generally fulfil a great need in the art for a relatively simple dosimeter and positioning apparatus which can be used with laser tools for reliably and consistently achieving excellent results.

SUMMARY OF THE INVENTION

According to the present invention there is provided an apparatus for positioning a laser tool, comprising means for aligning the laser tool relative to an object to be treated with laser beams from the laser tool, and means for accurately determining multiple different distances from an output tip of the laser tool to the object. The aligning means will preferably include a flat body and means for securing the flat body to the tip of the laser tool, while the determining means will preferably be adjustable and include an incremented member and means for selectively securing the incremented member to the flat body in a plurality of predetermined positions.

According to the invention there is also provided a kit of components for accurately positioning and utilizing a laser tool, the kit comprising means for positioning the laser tool in a plurality of predetermined positions relative to an object to be treated with laser beams from the laser tool, a set of predetermined specifications for achieving a variety of desired treatment effects with the laser tool, and a set of blank forms to be completed with results of actual experimentation and treatment operations for generating additional specifications with which desired treatment effects may be consistently achieved.

The positioning means will preferably comprise an adjustable distance guide adapted to be secured to the laser tool in a predetermined alignment, and which is also adapted to be selectively, readily adjusted into a plurality of predetermined positions.

The invention also encompasses methods for using the positioning apparatus and the kit of components as discussed above.

It is an object of the present invention to provide a relatively simple and inexpensive positioning device which can be used in combination with a laser tool for reliably and consistently achieving a variety of treatment effects with the laser tool.

It is an another object of the present invention to provide such a device which can be manipulated together with a medical laser using one hand.

It is still another object of the present invention to provide such a device which can be readily adapted for use with different laser tools, and which includes inexpensive and selectively replaceable components so that the device can be readily adapted for accurately achieving a wide variety of operations with the laser tools.

Yet another object of the present invention is to provide such a device which can be readily and easily adjusted and secured to a laser tool without the use of tools.

Other objects, advantages and salient features of the present invention will become apparent from the following detailed description which, when taken into conjunction with the annexed drawings, discloses preferred embodiments of the present invention.

BRIEF DESCRIPTION OF THE DRAWINGS

FIG. 1 is a front perspective view of a positioning device according to the first embodiment of the invention, the positioning device being connected to a laser tool.

FIG. 2 is a front perspective view of a flat body portion of the positioning device shown in FIG. 1.

FIG. 3 is an incremented member of the positioning device shown in FIG. 1.

FIG. 4 is an adapter member of the positioning device of FIG. 1.

FIG. 5 is a front perspective view of a conventional medical laser having a hand manipulatable laser tool mounted on an articulated arm.

FIG. 6 is a front elevational view of a positioning device according to second embodiment of the invention.

DETAILED DESCRIPTION OF PREFERRED EMBODIMENTS

Referring to FIGS. 1-4 there is shown a first preferred embodiment of a laser tool positioning device 2 according to a first preferred embodiment of the invention. In FIG. 1 the positioning device 2 is shown attached to a hand piece 1 of a laser tool, such as the medical laser 100 shown in FIG. 5.

The positioning device 2 generally includes a flat body 4, an adapter 6 for securing the flat body 4 to the laser hand piece 1, and an incremented member 8 which can be selectively secured to the flat body 4 in a plurality of positions for indicating a distance between the output tip of the laser hand piece 1 and an object to be treated, such as a skin lesion 10 shown in FIG. 1.

With reference to FIGS. 1 and 2, the flat body 4 is preferably in the form of a substantially L-shape member having a plurality of openings 12, 14, 16 defined vertically therethrough. The opening 12 is preferably threaded and adapted to receive a threaded end 18 (see FIG. 4) of the adapter 6. The opening 12 is preferably defined in the shorter arm of the L-shape flat body 4.

The openings 14, 16 are each adapted to snugly and slidably receive the incremented member 8 therethrough and are provided at opposite ends of the longer arm of the L-shape flat body 4.

Besides the threaded end 18, the adapter 6 also preferably includes an opposite threaded end 20 adapted to be secured to the output tip of the laser tool 1 and a flange 22 between the threaded ends to assure that the adapter will not be inserted too far into flat body 4 or into the laser tool 1. As will be understood, the flange 22 functions as a stopper or marker for readily achieving a proper alignment between the flat body 4 and the laser tool 1.

There will preferably be provided several of the adapters 6, each of which will have a different sized threaded end 20 so that the positioning device 2 can be used with different laser tools.

The incremented member 8 is preferably constructed as a rod adapted to be slidably received in either of the holes 14, 16 in the flat body 4. The rod has an engagement tip 30 which is adapted to engage the surface of an object to be treated (such as a skin having the lesion 10 formed therein), a plurality of recesses 32 defined along its length, and a plurality of reference markings 34 also defined along its length for accurately indicating respective distances between the tip 30 and the output lens of the laser tool 1 having the device 2 secured thereto when the member 8 is secured to the flat body 4 in various positions corresponding to the recesses 32. The device 2 will preferably include several of the incremented members 8, each of which will have a different length than the others for measuring a different range of distances than the other members. For example a device 2 could be provided with four of the incremented members 8, a first of which would measure from 0-100 mm, the second from 100-200 mm, the third from 200-300 mm, and the fourth from 300-400 mm. As shown in FIGS. 1 and 2, the hole 14 is closer to the hole 12 (and thus the laser tool 1) than is the hole 16. Depending on the length of the incremented member 8 which is chosen, corresponding to a distance required for a given operation, it will be secured in either of the holes 14 or 16. Particularly, if the member 8 is relatively short, such as less than or equal to 100 mm, it will be placed in the hole 14 closer to the laser tool 1, and if a longer incremented member is used it will be secured within the holes 16. Greater control can be achieved when the incremented member is positioned closer to the laser tool 1, but if a larger treatment distance is to be utilized it is necessary to locate the member 8 further away from the laser tool 1 to avoid any contact between the incremented member and a diverging laser beam from the laser tool. In light of such understanding, the holes 14, 16 could have different sizes, and the various incremented members 8 would have a size corresponding to either hole 14 or hole 16, whereby the operator would always insert the members 8 into the proper hole 14 or 16.

The recesses 32 may be formed as angular grooves about the incremented member 8 and are specifically adapted to engage by a biasing mechanism or means provided within the flat body 4 (discussed further hereinbelow) for stably, yet resiliently securing the incremented 8 in several predetermined positions along its length.

The biasing mechanism or means 24, 26, 28, 29 is preferably provided within the flat body 4 and is associated with each of the holes 14, 16 for resiliently securing the incremented 8 at various positions along its length. Although FIG. 2 shows the biasing means only in relation to hole 16, it will be understood that an identical means as used in relation to the hole 14. The biasing means preferably includes a ball 24, a spring 26 and an allen screw 28 secured in a another hole 29 which extends horizontally into the flat body 4 such that it intersects the hole 16 perpendicularly. The hole 29 will have a reduced diameter immediately before it intersects the hole 16, while the ball 24 will be sized such that it slides easily within the larger diameter portion of the hole 29 but cannot fully fit through the smaller diameter portion of the hole 29 into the hole 16. In this way a portion of the ball 22 will resiliently project in to the hole 16 under the bias of the spring 26 where it will engage the incremented member 8.

As discussed above, the incremented member 8 has a cross sectional size just smaller than the diameter of the holes 14, 16 so that the member 8 can be slidably supported within holes 14, 16 through the surface contact between the member 8 and the walls of the holes 14, 16 and through the additional pressure provided by the biasing means 24-29, but the member 8 can be easily slid through the holes 14, 16 by pressing on either end of the member 8.

Additionally, when the ball 24 of the biasing means stably engages one of the recesses 32 an additional amount of force will be required to slide the member 8 out of such engagement. As will be understood, such arrangement is desirable because it avoids the possibility of the incremented member 8 unintentionally sliding out of position while an operation is being preformed.

The flat body 4 will also preferably have slots 36, 38 defined in an upper surface thereof and which respectively intersect with the upper ends of the hole 14, 16. The slots 36, 38 facilitate accurate viewing of the reference characters 34 provided on the incremented member.

The several components of the positioning device 2 may be of any appropriate materials such as aluminum and/or plastics.

The device 2 may optionally include disposable sleeves 31 which can be provided over the engagement tip 30 of the incremented member 8 and disposed of after an operation has been preformed. Such sleeves 31 are particularly desirable for use when a medical operation is being preformed to avoid cross contamination between patients. Alternatively, the entire incremented members 8 or the tips 30 thereof could be sterilized after each use.

Although the body 4 of the preferred embodiment has been described as flat, the invention is not so limited. Rather the body 4 may be of any construction which achieves accurate alignment between the incremented member 8 and the laser tool 1. Similarly, the incremented member could be in other appropriate shapes, such as a rotating cam.

Method of Use

In use, an operator will initially select an appropriate adapter 6 and an appropriate incremented member 8 to be used with the flat body 4 and a given laser tool 1 for performing a given procedure, as discussed further below. The flat body 4 is secured to the laser tool 1 in a proper alignment using the adapter 6, after which the incremented member is slid within the proper hole 14 or 16 so that the engagement tip 30 projects an appropriate distance below the laser tool 1. The operator may then preform the given operation after the laser tool 1 and positioning device 2 are moved into an appropriate position relative to an object to be treated, i.e., such that the engagement tip 30 of the incremented member 8 engages the object.

According to another important aspect of the invention, a set of predetermined specifications for reliably achieving a desired variety of treatment effects with various laser tools will be provided together with the positioning device 2. Such predetermined specifications will, for example, define appropriate target distances, appropriate laser power outputs, and/or appropriate movement speeds at which a given medical laser (such as a $CO_2$ laser, a ruby laser, etc.; is to be used for achieving various desired tissue effects (discussed further hereinbelow) on various sized tissue samples.

Additionally, a set of blank forms, such as those in Tables I-V below will be provided, which forms may be completed with the results of actual experimentation and treatment operations for generating additional specifications with which desired treatment effects may be reliably achieved. Some tissue effects which the inventor has achieved using a $CO_2$ medical laser are as follows.

Initially, when the laser is operated in the focused continuous wave mode, i.e., for making incisions with the laser beam output focused at the point of tissue contact, various depths of incision (through the epidermis layer, through the mid dermis layer, etc.) will be achieved by the laser for various given outputs and various movement speeds of the laser tool relative to the tissue being treated.

Many other tissue effects may be achieved by utilizing the $CO_2$ laser in its pulsed vaporization mode (i.e., using a non-cutting defocused beam), which other effects include the following. (all effects resulting from a single laser pulse)

Opalescense 1 (OP1)

This the mildest effect, defined as slight whitening (blanching or opalescense) of tissue in response to firing the laser beam. The balanched area will not have well defined borders.

This effect is useful for treating flat skin lesions such as benign epidermal pigmented lesions and in resurfacing of skin (e.g. scars, wrinkles). Its effectiveness may not be as efficient as OP2 below. This OP1 effect is characterized by that it will not simply wipe off using a wet cotton applicator (as OP2 does).

Opalescense 2 (OP2)

Is whitening (blanching or opalescense) of tissue with well defined borders but without "blistering" or shrinkles of skin seen in OP3. This effect is more useful for the same indications listed above under OP1 (pigmented lesions, scars). Additionally this OP2 does have a mild hemostatic effect in cases of slight bleeding.

Opalescense 3 (OP3)

This is whitening of skin with striking skin contraction and has very well defined borders. The contracting skin lines appear radiating from the center similar to "wheel spikes". This is effective for hemostasis and for epidermal separation of a raised skin lesion such as a large seborrheic keratosis or a wart. This effect may be too strong for flat skin lesions (such as lentigos) as it will leave pink flat marks on the skin for considerable time. For such lesions OP2 and OP4 will be a better alternative (especially for lesions located on the hands). OP3, when obtained at longer distance with a larger spot size, has a characteristic "hissing sound".

Opalescense 4 (OP4)

This is a very unique tissue effect that can be totally missed or may have never been detected by many $CO_2$ laser surgeons who did not have the opportunity to observe $CO_2$ laser tissue effects at increasing distances. In a slow step wise, manner OP4 is obtained at a defocusing distance shorter than OP3 and longer than charring 1. This effect can be described as white crusting (or burning of the skin with a white crust) and is obtained at a defocusing distance shorter than OP3 and longer than charring 1. This effect can be described as white crusting (or burning of the skin with a white crust) accompanied by a characteristic "popping" sound (similar to popcorn sound) and characterized by its small size, usually 1-2 mm. This white crust is identical in appearance to the white crust tissue effect obtained by using a more expensive pigmented candela or ultra pulse coherent laser tool. OP4 is the step before charring although charring 1 CH1 may have a larger spot size (against to what is expected). Also, contrary to what is expected, OP4, that occurs at distances between OP3 and charring 1, causes less tissue penetration, less collateral heat damage and less pain perception that OP3. OP4 occurs at a narrow zone of distances that can be easily missed. The spot size also suddenly drops from several mm at OP3 distance to ½-2 mm at the OP4 distance and then increases again at next charring 1 distance.

Charring 1 (CH1)

This is the first degree of charring where the color of vaporized tissue is black. CH1 stage is easy to identify because of its black color and because it occurs at a distance immediately shorter than the OP4 effect. It is suitable for treatment of raised (but not thick or deep) lesions in one pass only.

Charring 2 (CH2)

This is an intermediate stage of penetration depth between CH1 and CH3. It will remove a moderately thick seborrheic keratosis in two passes.

Charring 3 (CH3)

This has the deepest penetration when high power and long exposure times are used. An attempt to quantify the depth of penetration will be measuring by the depth of the crater produced with a depth gauge instrument. The Burke Depth Ruler distributed by Stackhouse Laser Inc., Riverside, Calif., as an example, will measure depth in one mm increments, other gauges with higher precision are also available on the market.

According to the invention, the above and other desired tissue effects may be achieved using the positioning device 2 in light of a set of predetermined specifications provided with the device 2 or in light of additional specifications which may be generated using forms as set forth in Tables I-V below.

Table I is a blank form which permits a practitioner to easily record various tissues effects which the practitioner has actually achieved using a given $CO_2$ medical laser with a given size lens, and with the laser operating at given power outputs and given exposure times on various tissue spot sizes and with the device 2 set at various distances. As will be understood, it will be necessary for the practitioner to utilizes a separate form as set forth in Table I for each distance setting of the positioning device 2.

Table II is the form of Table I which has been completed for a distance setting of 100 mm, using a coherent $CO_2$ laser machine with a 1 mm lens. As indicated in Table II, it may be possible to achieve desired tissue effects only with certain power levels and exposure times, while different tissue effects may be achieved for the same power output and exposure time when treating different spot sizes.

Tables III and IV are two additional blank forms which the operator would utilize by filling in a few favorite parameters which the practitioner has confirmed through actual experimentation and operations, and which would preferably be extracted from many of the completed forms such as shown in Table II.

Table V is the form of Table IV which has been completed for a coherent $CO_2$ laser machine with a 1 mm lens and with opalescense 3 (OP3) as the desired tissue effect. The completed forms of Tables III and IV will be the final specifications which the practitioner will frequently utilize in his/her daily practice.

An exemplary procedure for utilizing the positioning device 2 together with the standardized specifications or with other specifications generated utilizing Tables I-V is as follows.

Initially, the practitioner will chose the desired tissue effect such as OP1, CH1, etc. The practitioner will then determine the size of the skin sample/lesion to be treated, and will chose a spot size that preferably does not exceed the actual determined size of the lesion. It is preferable to chose a spot size smaller than the actual size of the lesion to avoid damaging the normal tissue which surrounds the lesion, while the practitioner can administer several laser pulses to completely fill the lesion.

Next, the practitioner will preferably choose the shortest exposure time that will provide the desired tissue effect for the given spot size. The shorter the exposure time, the less is the collateral heat damage to surrounding normal tissue.

The practitioner then sets the positioning device 2 at the proper distance setting by selecting the appropriate incremented member 8, inserting it into the appropriate hole 14 or 16, and sliding the member into the hole until the proper distance is achieved; the positioning device 2 is attached to the laser tool 1 using an appropriate adapter 6, if the device 2 was not previously attached to the laser tool; the power output and exposure time are then set on the laser tool; and the practitioner performs the operation.

If the resulting tissue effect level is lower than what is expected, which may result from several factors such as over heating of the laser tube of the laser tool, the practitioner can step up the parameters slightly by either increasing the power output by a small number of watts (1 or 2) or by decreasing the distance setting by a small one or two increments (such as 1-10 mm). Alternatively, the practitioner could increase the exposure time, although such an increase is not preferred because it has a greater likelihood of resulting in damage to adjacent tissue.

Similarly, if the resulting tissue effect was higher or deeper than what the practitioner expected, the practitioner could step down one or more of the controlling parameters by small amount the next time the practitioner preforms a similar operation.

Referring to FIG. 6 of the drawings there is shown a second embodiment of a position device according to the present invention, the positioning device comprises a set of several different sized distance guides 102, 104, 106, 108, each of which may be selectively attached to the output tip of laser tool 1. The distance guide 102 will have a length corresponding to the focal length of the output lens of the laser tool 1, and will thus be identical to the conventional distance guides which are known to be provided by laser manufacturers such as the guide 101 shown in FIG. 5. The other distance guides 104, 106, 108 will have different lengths, all of which are greater than the length of the guide 102, and which will correspond to various preferred distances for achieving desired effects other than cutting. For example, the guide 104 may have a length 5 mm greater than that of the guide 102, the guide 106 may have a length 15 mm greater than that of the guide 102, and the guide 108 may have a length 30 mm greater than that of the guide 102.

As shown, the upper end of each of the guides 102-108 is adapted to be secured within the output tip of the laser tool. The upper ends of the guides 102-108 and the lower ends of the laser tool 1 may be threaded for achieving a secure connection therebetween, or the upper ends of the guides 102-108 may be adapted to simply be snap fitted to the lower end of laser tool.

Although there are only four of the distance guides 102-108 shown in FIG. 6, it will be understood that many more different guides could be utilized according to the second embodiment of the invention.

Although there have been described what are at present considered to be the preferred embodiments of the present invention, it will be understood that invention can be embodied in other specific forms without departing from the spirit or essential characteristics thereof. For example, it is contemplated that a non-contact distance measuring device could be provided for use in combination with a laser tool, which non-contact measuring device would measure a distance between the laser tool and an object using an ultrasonic, infrared, laser, etc. distance measuring device. Such non-contact measuring devices would be less bulky and cumbersome than the positioning device 2 shown in FIG. 1, but would not provide the desirable stability associated with the contact type positioning device 2.

Further, the forms shown in Tables I-V could be replaced with a software program into which standardized specifications, experimental results, and actual operational results are entered into a data file, after which a practitioner could address such data file with a desired treatment effect and/or desired spot size, and the program would output the necessary parameters (distance, exposure time, power output, etc.), which the operator would then set to achieve the desired treatment effect. Such program could be incorporated in a hand held calculator type device.

Relatedly, a program as discussed above could be incorporated in a much larger apparatus for automatically/robotically controlling a laser tool to achieve various desired treatment effects.

The present embodiments are therefore considered in all aspects as illustrative and not restrictive. The scope of the invention is indicated by the appended claims rather than by the foregoing description.

TABLE I

| | | \multicolumn{8}{c}{$CO_2$ Laser: Treatment Parameters} |
|---|---|---|---|---|---|---|---|---|---|

| | | \multicolumn{8}{c}{Machine: Lens:} |

| | Exposure | 1 watt | | 2 watts | | 3 watts | | 4 watts | |
|---|---|---|---|---|---|---|---|---|---|
| Distance | Time (sec) | Tissue Effect | Spot Size, mm | Tissue Effect | Spot Size, mm | Tissue Effect | Spot Size, mm | Tissue Effect | Spot Size, mm |
| mm | .05" | | | | | | | | |
| | .1" | | | | | | | | |
| | .2" | | | | | | | | |
| | .5" | | | | | | | | |

| | Exposure | 5 watts | | 6 watts | | 7 watts | | 8 watts | |
|---|---|---|---|---|---|---|---|---|---|
| Distance | Time (sec) | Tissue Effect | Spot Size, mm | Tissue Effect | Spot Size, mm | Tissue Effect | Spot Size, mm | Tissue Effect | Spot Size, mm |
| mm | .05" | | | | | | | | |
| | .1" | | | | | | | | |
| | .2" | | | | | | | | |
| | .5" | | | | | | | | |

| | Exposure | 9 watts | | 10 watts | | 11 watts | | 12 watts | |
|---|---|---|---|---|---|---|---|---|---|
| Distance | Time (sec) | Tissue Effect | Spot Size, mm | Tissue Effect | Spot Size, mm | Tissue Effect | Spot Size, mm | Tissue Effect | Spot Size, mm |
| mm | .05" | | | | | | | | |
| | .1" | | | | | | | | |
| | .2" | | | | | | | | |
| | .5" | | | | | | | | |

| | Exposure | 13 watts | | 14 watts | | 15 watts | | 16 watts | |
|---|---|---|---|---|---|---|---|---|---|
| Distance | Time (sec) | Tissue Effect | Spot Size, mm | Tissue Effect | Spot Size, mm | Tissue Effect | Spot Size, mm | Tissue Effect | Spot Size, mm |
| mm | .05" | | | | | | | | |
| | .1" | | | | | | | | |
| | .2" | | | | | | | | |
| | .5" | | | | | | | | |

| | Exposure | 17 watts | | 18 watts | | 19 watts | | 20 watts | |
|---|---|---|---|---|---|---|---|---|---|
| Distance | Time (sec) | Tissue Effect | Spot Size, mm | Tissue Effect | Spot Size, mm | Tissue Effect | Spot Size, mm | Tissue Effect | Spot Size, mm |
| mm | .05" | | | | | | | | |
| | .1" | | | | | | | | |
| | .2" | | | | | | | | |
| | .5" | | | | | | | | |

| | Exposure | SP 1 | | SP 2 | | SP 3 | | SP 4 | |
|---|---|---|---|---|---|---|---|---|---|
| Distance | Time (sec) | Tissue Effect | Spot Size, mm | Tissue Effect | Spot Size, mm | Tissue Effect | Spot Size, mm | Tissue Effect | Spot Size, mm |
| mm | .05" | | | | | | | | |
| | .1" | | | | | | | | |
| | .2" | | | | | | | | |
| | .5" | | | | | | | | |

TABLE II

CO2 Laser: Treatment Parameters  100 mm Distance
Machine: Coherent  Lens: 1 mm

| Distance | Exposure Time (sec) | 1 watt Tissue Effect | 1 watt Spot Size, mm | 2 watts Tissue Effect | 2 watts Spot Size, mm | 3 watts Tissue Effect | 3 watts Spot Size, mm | 4 watts Tissue Effect | 4 watts Spot Size, mm |
|---|---|---|---|---|---|---|---|---|---|
| mm | .05" | | | 0 | 0 | | | | |
| 100 mm | .1" | | | 0 | 0 | | | | |
| Distance | .2" | | | OP1 | 3 mm | | | | |
| | .5" | | | OP1 | 2 mm | | | | |

| Distance | Exposure Time (sec) | 5 watts Tissue Effect | 5 watts Spot Size, mm | 6 watts Tissue Effect | 6 watts Spot Size, mm | 7 watts Tissue Effect | 7 watts Spot Size, mm | 8 watts Tissue Effect | 8 watts Spot Size, mm |
|---|---|---|---|---|---|---|---|---|---|
| mm | .05" | 0 | 0 | 0 | 0 | 0 | 0 | | |
| 100 mm | .1" | 0 | 0 | 0 | 0 | 0 | 0 | | |
| Distance | .2" | 0 | 0 | OP1 | 4 mm | OP1 | 3 mm | | |
| | .5" | OP2 | 4 mm | OP2 | 4 mm | OP3 | 5 mm | | |
| | | | | OP3 | | OP2 | 3 mm | | |

| Distance | Exposure Time (sec) | 9 watts Tissue Effect | 9 watts Spot Size, mm | 10 watts Tissue Effect | 10 watts Spot Size, mm | 11 watts Tissue Effect | 11 watts Spot Size, mm | 12 watts Tissue Effect | 12 watts Spot Size, mm |
|---|---|---|---|---|---|---|---|---|---|
| mm | .05" | | | OP1 | 3 mm | | | | |
| 100 mm | .1" | | | OP1 | 4 mm | | | | |
| Distance | .2" | | | OP1 | 4 mm | | | | |
| | .5" | | | OP3 | 6 mm | | | | |

| Distance | Exposure Time (sec) | 13 watts Tissue Effect | 13 watts Spot Size, mm | 14 watts Tissue Effect | 14 watts Spot Size, mm | 15 watts Tissue Effect | 15 watts Spot Size, mm | 16 watts Tissue Effect | 16 watts Spot Size, mm |
|---|---|---|---|---|---|---|---|---|---|
| mm | .05" | | | | | 0 | 0 | | |
| 100 mm | .1" | | | | | 0 | 0 | | |
| Distance | .2" | | | | | OP3 | 8 mm | | |
| | .5" | | | | | OP3 | 10 mm | | |

| Distance | Exposure Time (sec) | 17 watts Tissue Effect | 17 watts Spot Size, mm | 18 watts Tissue Effect | 18 watts Spot Size, mm | 19 watts Tissue Effect | 19 watts Spot Size, mm | 20 watts Tissue Effect | 20 watts Spot Size, mm |
|---|---|---|---|---|---|---|---|---|---|
| mm | .05" | | | | | | | 0 | 0 |
| 100 mm | .1" | | | | | | | 0 | 0 |
| Distance | .2" | | | | | | | OP2-3 | 8 mm |
| | .5" | | | | | | | CH2 | 5 mm |
| | | | | | | | | OP3 | 3 mm |

| Distance | Exposure Time (sec) | SP 1 Tissue Effect | SP 1 Spot Size, mm | SP 2 Tissue Effect | SP 2 Spot Size, mm | SP 3 Tissue Effect | SP 3 Spot Size, mm | SP 4 Tissue Effect | SP 4 Spot Size, mm |
|---|---|---|---|---|---|---|---|---|---|
| mm | .05" | 0 | 0 | OP2 | 4 mm | 0 | 0 | 0 | 0 |
| 100 mm | .1" | OP1 | 3 mm | | | 0 | 0 | OP1 | 3 mm |
| Distance | .2" | OP1 | 3 mm | OP2 | 3 mm | 0 | 0 | OP2 | 6 mm |
| | .5" | OP3 | 5 mm | 4 mm | OP 1 | 3 mm | | | |
| | | OP3 | 6 mm | | | | | | |

TABLE III

| Level of Tissue Effect | TISSUE EFFECT Name and Description of Tissue Effect | Code Name | SPOT SIZE In Millimeters | PARAMETERS Exposure Time in Seconds | Power in Watts | Distance in mm |
|---|---|---|---|---|---|---|
| Level 1 | Opalescense 1 | OP1 | 1 mm | | | |
| | | | 2 mm | | | |
| | | | 3 mm | | | |
| | | | 10 mm | | | |
| Level 2 | Opalescense 2 | OP2 | 1 mm | | | |
| | | | 2 mm | | | |
| | | | 3 mm | | | |
| | | | 10 mm | | | |
| Level 3 | Opalescense 3 | OP3 | 1 mm | | | |
| | | | 2 mm | | | |
| | | | 3 mm | | | |
| | | | 10 mm | | | |
| Level 4 | Opalescense 4 | OP4 | 1 mm | | | |
| | | | 2 mm | | | |
| | | | 3 mm | | | |
| | | | 10 mm | | | |
| Level 5 | Charring 1 | CH1 | 1 mm | | | |
| | | | 2 mm | | | |
| | | | 3 mm | | | |

TABLE III-continued

| TISSUE EFFECT | | | SPOT SIZE | PARAMETERS | | |
|---|---|---|---|---|---|---|
| Level of Tissue Effect | Name and Description of Tissue Effect | Code Name | In Millimeters | Exposure Time in Seconds | Power in Watts | Distance in mm |
| Level 6 | Charring 2 | CH2 | 1 mm | | | |
| | | | 2 mm | | | |
| | | | 3 mm | | | |
| Level 7 | Charring 3 | CH3 | 1 mm | | | |
| | | | 2 mm | | | |
| | | | 3 mm | | | |

TABLE IV

| | Tissue Effect: | | |
|---|---|---|---|
| SPOT SIZE | Time sec. | Power watt | Distance mm |
| 1 mm | | | |
| 2 mm | | | |
| 3 mm | | | |
| 4 mm | | | |
| 5 mm | | | |
| 6 mm | | | |
| 7 mm | | | |
| 8 mm | | | |
| 9 mm | | | |
| 10 mm | | | |

TABLE V

| | Tissue Effect: OP3 | Coherent 1 mm lens | |
|---|---|---|---|
| SPOT SIZE | Time sec. | Power watt | Pain 1°–3° |
| 1 mm | | | |
| 2 mm | .05" | SP4 | 15 |
| | .05" | 5 w | 20 ? |
| 3 mm | .2" | 20 w | 250 |
| 4 mm | .5" | 6 w | 100 |
| | .5" | SP2 | 100 |
| 5 mm | .5" | 7 w | 100 |
| 6 mm | .5" | 10 w | 100 |
| | .5" | SP1 | 100 |
| 7 mm | | | |
| 8 mm | .2" | 15 w | 100 |
| | .1" | 20 w | 100 |
| 9 mm | | | |
| 10 mm | .5" | 20 w | 200 |
| | .5" | 15 w | 100 |

I claim:

1. Positioning apparatus for being selectively connected to a laser tool to position the tool, said positioning apparatus comprising:

distance determining means adapted to be connected to a laser tool for accurately determining multiple different distances from an output tip of the laser tool to an object to be treated with the laser tool; and mean for fixing the distance determining means to said laser tool in a predetermined alignment;

said distance determining means being adjustable and including an incremented rod having a plurality of recesses defined in spaced intervals along its length;

said fixing means including biasing means for resiliently engaging an outer surface of said incremented rod by individually engaging said recesses as said rod is moved relative to said securing means for thereby selectively fixing said incremented rod in a plurality of positions relative to said laser tool; and said fixing means further includes a flat body and means for securing the flat body to the output tip of the laser tool, said flat body having an opening defined therethrough which is adapted to slidably receive said incremented rod and said biasing means being connected to said flat body.

2. Apparatus according to claim 1, wherein said increment rod has a tip which is adapted to engage the object to be treated and a plurality of distance markings provided in spaced intervals therealong corresponding to respective distances from said tip to said markings.

3. Apparatus according to claim 1 wherein said flat body has a slot defined in an upper surface thereof and extending into said opening, said incremented rod has a plurality of distance markings provided in spaced intervals therealong, and said rod is adapted to be fitted into said opening such that said distance markings on said rod can be easily viewed in said slot.

4. A kit of components for accurately positioning and utilizing a laser tool, comprising:

means for positioning a laser tool in a plurality of predetermined positions relative to an object to be treated with the laser tool;

predetermined specifications for achieving a variety of desired treatment effects with the laser tool disposed at various positions relative to the object; and a set of blank forms to be completed with results of actual experimentation and treatment operations for generating additional specifications with which desired treatment effects may be achieved;

said positioning means comprising and adjustable distance guide and means for securing the distance guide to the laser tool;

said distance guide comprising a plurality of differently sized incremented members, and means for individually, resiliently positioning said incremented members in multiple positions relative to the laser tool, and said securing means comprises a plurality of different sized adapters for securing said distance guide to different sized laser tools.

5. A kit according to claim 4, wherein said distance guide further comprises a flat body having an opening defined therethrough and which is adapted to individually, slidingly receive said incremented members.

6. A kit according to claim 5, wherein said distance guide further comprises a biasing means for resiliently engaging outer surfaces of said incremented members and which permits the incremented members to be stably slid relative to the flat body.

7. A kit according to claim 6, wherein each of said incremented members is a rod having a plurality of recesses defined in spaced intervals along its length, and said biasing means is adapted to individually engage said recesses as said rod is moved relative to the flat body.

8. Apparatus according to claim 5, wherein, each of said incremented members has a plurality of distance markings provided in spaced intervals therealong, said flat body has a slot defined in an upper surface thereof which extends into said opening defined through the flat body, and each of said incremented members is adapted to be fitted into said openings such that said distance markings thereon can be easily viewed in said slot.

9. A kit according to claim 4, including predetermined specifications for multiple different laser tools and blank forms corresponding to multiple different laser tools.

10. A kit according to claim 4, including a plurality of disposable tip members which are adapted to be fitted over tips of said incremented members for engaging an object to be treated.

* * * * *